(12) United States Patent
Al Khunaizi et al.

(10) Patent No.: US 11,840,505 B1
(45) Date of Patent: Dec. 12, 2023

(54) PROCESS AND CRACKING CATALYST FOR CRACKING BUTENES TO PRODUCE LIGHT OLEFINS

(71) Applicant: Saudi Arabian Oil Company, Dhahran (SA)

(72) Inventors: Hashim N Al Khunaizi, Qatif (SA); Furqan F Aljumah, Dhahran (SA)

(73) Assignee: Saudi Arabian Oil Company, Dhahran (SA)

( * ) Notice: Subject to any disclaimer, the term of this patent is extended or adjusted under 35 U.S.C. 154(b) by 0 days.

(21) Appl. No.: 17/930,089

(22) Filed: Sep. 7, 2022

(51) Int. Cl.
  C07C 4/06 (2006.01)
  B01J 29/46 (2006.01)
  B01J 31/02 (2006.01)

(52) U.S. Cl.
  CPC ............... C07C 4/06 (2013.01); B01J 29/46 (2013.01); B01J 31/0257 (2013.01); C07C 2523/745 (2013.01); C07C 2523/755 (2013.01); C07C 2529/40 (2013.01); C07C 2529/46 (2013.01); C07C 2531/02 (2013.01)

(58) Field of Classification Search
  CPC ............... C07C 4/06; C07C 2523/745; C07C 2523/755; C07C 2529/40; C07C 2529/46; C07C 2531/02; C07C /; B01J 29/46; B01J 31/0257
  See application file for complete search history.

(56) References Cited

U.S. PATENT DOCUMENTS

| 9,611,432 B2 | 4/2017 | Xu et al. |
| 10,464,053 B2 * | 11/2019 | Nesterenko .......... B01J 29/7049 |
| 2017/0087540 A1 * | 3/2017 | Llias ....................... B01J 29/405 |
| 2019/0002767 A1 * | 1/2019 | Dries .................... B01J 29/7015 |
| 2019/0022633 A1 * | 1/2019 | Al-Khattaf ............. B01J 35/002 |
| 2020/0140354 A1 * | 5/2020 | Mcguire ............... B01J 37/0009 |
| 2022/0098493 A1 | 3/2022 | Akah et al. |

FOREIGN PATENT DOCUMENTS

WO   2004071656 A1   8/2004

OTHER PUBLICATIONS

Li et al., "Effect of Impregnating Fe into P-Modified HZSM-5 in the Coupling Cracking of Butene and Pentene", Industrial & Engineering Chemistry Research, vol. 54, pp. 1796-1804, 2015.

* cited by examiner

Primary Examiner — Ali Z Fadhel
(74) Attorney, Agent, or Firm — DINSMORE & SHOHL LLP (57) ABSTRACT

A process for cracking olefins to produce propylene, ethylene, or both, includes providing a feed stream that includes mixed butenes and contacting the feed stream with a cracking catalyst at reaction conditions that cause at least a portion of the mixed butenes in the feed stream to react to form propylene, ethylene, or both. The cracking catalyst includes zeolite particles formed from shape selective zeolite particles and an alumina binder. The cracking catalyst further includes at least one transition metal oxide impregnated onto the zeolite particles, where the at least one transition metal oxide can be iron oxide, nickel oxide, or a combinations of these. The cracking catalyst with the iron oxide, nickel oxide, or both increases conversion of mixed butenes to propylene, ethylene, or both alone or in combination with a metathesis upstream of the cracking catalyst, as compared to conventional cracking catalysts.

15 Claims, 3 Drawing Sheets

PROCESS AND CRACKING CATALYST FOR CRACKING BUTENES TO PRODUCE LIGHT OLEFINS

BACKGROUND

Field

The present disclosure relates to processes and catalysts for processing hydrocarbon materials and, in particular, processes and catalyst compositions for cracking butenes to produce propylene and ethylene

Technical Background

The worldwide increasing demand for light olefins remains a major challenge for many integrated refineries. In particular, the production of some valuable light olefins, such as ethylene and propylene, has attracted increased attention as pure olefin streams are considered the building blocks for polymer synthesis. The production of light olefins depends on several process variables, such as the feed type, operating conditions, and the type of catalyst. Despite the options available for producing a greater yield of propylene and light olefins, intense research activity in this field is still being conducted. For example, light olefins are typically produced through thermal cracking (or steam pyrolysis) of petroleum gases and distillates, such as naphtha, kerosene, or gas oil. Light olefins may also be produced through fluid catalytic cracking processes. However, these processes generally produce a significant amount of lower value component streams, such as C4 streams comprising mixed butenes, and mixed butanes, which have lower value compared to ethylene and propylene.

SUMMARY

Accordingly, there is an ongoing need for cracking catalysts and processes for cracking C4-containing streams to produce greater yields of propylene and ethylene. The present disclosure is directed to cracking catalysts and processes for catalytic cracking of mixed butenes to produce greater yields of propylene and ethylene. The cracking catalyst of the present disclosure includes zeolite particles comprising a medium pore zeolite and an aluminum binder. The cracking catalyst further comprises iron oxide, nickel oxide, or iron oxide and nickel oxide impregnated onto the surfaces of the zeolite particles. The medium pore zeolite has a high silica to alumina molar ratio of greater than or equal to 500 and very low phosphorous content, such as less than or equal to 1000 parts per million by weight. The processes of the present disclosure include contacting a feed stream comprising mixed butenes with the cracking catalyst under reaction conditions sufficient to convert at least a portion of the mixed butenes to propylene, ethylene, or both. The cracking catalyst can also be used in conjunction with a metathesis catalyst to convert mixed butenes to propylene and ethylene through a combination of metathesis and catalytic cracking.

According to at least one aspect of the present disclosure, a process for cracking olefins to produce propylene, ethylene, or both, may include providing a feed stream comprising mixed butenes and contacting the feed stream with a cracking catalyst at reaction conditions that may cause at least a portion of the mixed butenes in the feed stream to react to form propylene, ethylene, or both. The cracking catalyst may comprise zeolite particles comprising a shape selective zeolite and an alumina binder. The cracking catalyst may further comprise at least one transition metal oxide impregnated onto the zeolite particles. The at least one transition metal oxide may be selected from the group consisting of iron oxide, nickel oxide, and combinations of these.

According to at least another aspect of the present disclosure, a cracking catalyst for cracking olefins to produce propylene, ethylene, or both may include a plurality of zeolite particles comprising ZSM-5 zeolite and an alumina binder; and nickel oxide, iron oxide, or both impregnated onto the surfaces of the zeolite particles.

Additional features and advantages of the aspects of the present disclosure will be set forth in the detailed description that follows and, in part, will be readily apparent to a person of ordinary skill in the art from the detailed description or recognized by practicing the aspects of the present disclosure.

BRIEF DESCRIPTION OF THE DRAWINGS

The following detailed description of the present disclosure may be better understood when read in conjunction with the following drawings in which.

When describing the simplified schematic illustrations of FIGS. 1-6, the numerous valves, temperature sensors, electronic controllers, and the like, which may be used and are well known to a person of ordinary skill in the art, may not be included. Further, accompanying components that are often included in systems such as those depicted in FIGS. 1-6, such as air supplies, heat exchangers, surge tanks, and the like also may not be included. However, a person of ordinary skill in the art understands that these components are within the scope of the present disclosure.

Additionally, the arrows in the simplified schematic illustrations of FIGS. 1-6 refer to process streams. However, the arrows may equivalently refer to transfer lines, which may transfer process steams between two or more system components. Arrows that connect to one or more system components signify inlets or outlets in the given system components and arrows that connect to only one system component signify a system outlet stream that exits the depicted system or a system inlet stream that enters the depicted system. The arrow direction generally corresponds with the major direction of movement of the process stream or the process stream contained within the physical transfer line signified by the arrow.

The arrows in the simplified schematic illustrations of FIGS. 1-6 may also refer to process steps of transporting a process stream from one system component to another system component. For example, an arrow from a first system component pointing to a second system component may signify "passing" a process stream from the first system component to the second system component, which may comprise the process stream "exiting" or being "removed" from the first system component and "introducing" the process stream to the second system component.

Reference will now be made in greater detail to various aspects, some of which are illustrated in the accompanying drawings.

DETAILED DESCRIPTION

The present disclosure is directed to cracking catalysts and processes for catalytic cracking of butenes to produce propylene, ethylene, or both. The cracking catalyst of the present disclosure comprises a plurality of zeolite particles comprising a shape selective zeolite, such as but not limited to ZSM-5 zeolite, and an alumina binder. The cracking catalyst further comprises at least one transition metal oxide impregnated onto the surface of the zeolite particles. The transition metal oxide can comprise nickel oxide, iron oxide, or iron oxide and nickel oxide impregnated onto the surfaces of the zeolite particles. The cracking catalyst can have a very low phosphorous content, such as less than or equal to 1000 parts per million by weight.

The cracking catalyst can be used to crack mixed butenes and other olefins to produce propylene, ethylene, or both. A process for cracking olefins to produce propylene, ethylene, or both can include providing a feed stream comprising mixed butenes and contacting the feed stream with the cracking catalyst at reaction conditions that cause at least a portion of the mixed butenes in the feed stream to react to form propylene, ethylene, or both. The cracking catalyst can include any of the cracking catalysts discussed in the present disclosure. The cracking catalyst and processes of the present disclosure can increase yield of propylene, ethylene, or both from cracking mixed butenes compared to other conventional cracking catalysts (e.g., unmodified zeolites).

As used in the present disclosure, the term "cracking" refers to a chemical reaction where a molecule having carbon-carbon bonds is broken into more than one molecule by the breaking of one or more of the carbon-carbon bonds; where a compound including a cyclic moiety, such as an aromatic, is converted to a compound that does not include a cyclic moiety; or where a molecule having carbon-carbon double bonds are reduced to carbon-carbon single bonds. As used in the present disclosure, the term "catalytic cracking" refers to cracking conducted in the presence of a catalyst. Some catalysts may have multiple forms of catalytic activity, and calling a catalyst by one particular function does not render that catalyst incapable of being catalytically active for other functionality.

As used in the present disclosure, the term "catalyst" refers to any substance that increases the rate of a specific chemical reaction, such as but not limited to cracking reactions.

As used in the present disclosure, the term "used catalyst" refers to catalyst that has been contacted with reactants at reaction conditions, but has not been regenerated in a regenerator. The "used catalyst" may have coke deposited on the catalyst and may include partially coked catalyst as well as fully coked catalysts. The amount of coke deposited on the "used catalyst" may be greater than the amount of coke remaining on the regenerated catalyst following regeneration. The "used catalyst" may also include catalyst that has a reduced temperature due to contact with the reactants compared to the catalyst prior to contact with the reactants.

As used in the present disclosure, the term "regenerated catalyst" refers to catalyst that has been contacted with reactants at reaction conditions and then regenerated in a regenerator to heat the catalyst to a greater temperature, oxidize and remove at least a portion of the coke or other organic contaminants from the catalyst to restore at least a portion of the catalytic activity of the catalyst, or both. The "regenerated catalyst" may have less coke or organic contaminants, a greater temperature, or both, compared to used catalyst and may have greater catalytic activity compared to used catalyst. The "regenerated catalyst" may have more coke and lesser catalytic activity compared to fresh catalyst that has not been contacted with reactants a cracking reaction zone and then regenerated.

As used throughout the present disclosure, the terms "butenes" or "mixed butenes" are used interchangeably and refer to combinations of one or a plurality of isobutene, 1-butene, trans-2-butene, or cis-2-butene. As used throughout the present disclosure, the term "normal butenes" refers to a combination of one or a plurality of 1-butene, trans-2-butene, or cis-2-butene. As used throughout the present disclosure, the term "2-butenes" refers to trans-2-butene, cis-2-butene, or a combinations of these.

As used throughout the present disclosure, the term "C4" refers to compositions or streams comprising compounds having 4 carbon atoms. The term "C4+" refers to compositions or streams comprising compounds having 4 or more than 4 carbon atoms. The term "C5+" refers to compositions or streams comprising compounds having 5 or more than 5 carbon atoms.

As used in the present disclosure, the term "directly" refers to the passing of materials, such as an effluent, from a first component of a processing system to a second component of the processing system without passing the materials through any intervening components or unit operations operable to change the composition of the materials. Similarly, the term "directly" also refers to the introducing of materials, such as a feed, to a component of the process system without passing the materials through any preliminary components operable to change the composition of the materials. Intervening or preliminary components or systems operable to change the composition of the materials include reactors and separators, but are not generally intended to include heat exchangers, valves, pumps, sensors, or other ancillary components required for operation of a chemical process.

As used in the present disclosure, the terms "downstream" and "upstream" refer to the positioning of components or unit operations of the processing system relative to a direction of flow of materials through the processing system. For example, a second component is considered "downstream" of a first component if materials flowing through the processing system encounter the first component before encountering the second component. Likewise, the first component is considered "upstream" of the second component if the materials flowing through the processing system encounter the first component before encountering the second component.

As used in the present disclosure, the term "effluent" refers to a stream that is passed out of a reactor, a reaction zone, or a separator following a particular reaction or separation. Generally, an effluent has a different composition than the stream that entered the reactor, reaction zone, or separator. It should be understood that when an effluent is passed to another component or system, only a portion of that effluent may be passed. For example, a slipstream may carry some of the effluent away, meaning that only a portion of the effluent may enter the downstream component or system. The terms "reaction effluent" and "reactor effluent" particularly refer to a stream that is passed out of a reactor or reaction zone.

The term "residence time" refers to the amount of time that reactants are in contact with a catalyst, at reaction conditions, such as at the reaction temperature.

As used in the present disclosure, the term "reactor" refers to any vessel, container, conduit, or the like, in which one or more chemical reactions, such as but not limited catalytic cracking reactions, may occur between one or more reactants optionally in the presence of one or more catalysts. One or more "reaction zones" may be disposed within a reactor. The term "reaction zone" refers to a volume where a particular chemical reaction takes place in a reactor.

As used in the present disclosure, the terms "separation unit" and "separator" refer to any separation device(s) that at least partially separates one or more chemical constituents in a mixture from one another. For example, a separation system selectively separates different chemical constituents from one another, forming one or more chemical fractions. Examples of separation systems include, without limitation, distillation columns, fractionators, flash drums, knock-out drums, knock-out pots, centrifuges, filtration devices, traps, scrubbers, expansion devices, membranes, solvent extraction devices, high-pressure separators, low-pressure separators, or combinations or these. The separation processes described in the present disclosure may not completely separate all of one chemical constituent from all of another chemical constituent. Instead, the separation processes described in the present disclosure "at least partially" separate different chemical constituents from one another and, even if not explicitly stated, separation can include only partial separation.

It should further be understood that streams may be named for the components of the stream, and the component for which the stream is named may be the major component of the stream (such as the component comprising the greatest fraction of the stream). It should also be understood that components of a stream are disclosed as passing from one system component to another when a stream comprising that component is disclosed as passing from that system component to another. For example, a disclosed "mixed butene stream" passing to a first system component or from a first system component to a second system component should be understood to equivalently disclose "mixed butenes" passing to the first system component or passing from a first system component to a second system component.

As previously discussed, greater value light olefins, such as propylene and ethylene, can be produced through steam cracking or fluidized catalytic cracking. However, these processes can produce a significant amount of lower value streams, one of which is a C4 stream comprising mixed butenes and butane, which have lower value compared to propylene and ethylene. In some cases, these C4 streams can be further catalytically cracked to convert mixed butenes from the C4 streams to additional propylene, ethylene, or both. Medium pore zeolites, such as ZSM-5, have been used to catalytically crack mixed butenes to propylene or ethylene. However, the yield of propylene, ethylene, or both from catalytically cracking butenes with zeolites have been limited. Therefore, an ongoing need exists for cracking catalysts and catalytic cracking processes that provide increased conversion of butenes to propylene, ethylene, or both to increase the yield of propylene, ethylene, or both.

The present disclosure is directed to cracking catalysts and catalytic cracking processes that increase the conversion of mixed butenes and the yield of propylene, ethylene, or both compared to conventional cracking catalysts. The processes of the present disclosure for catalytically cracking mixed butenes to produce propylene, ethylene, or both, includes providing a feed stream that includes mixed butenes and contacting the feed stream with a cracking catalyst at reaction conditions that cause at least a portion of the mixed butenes in the feed stream to react to form propylene, ethylene, or both. The cracking catalyst comprises zeolite particles that include a medium pore zeolite and an alumina binder. The cracking catalyst further includes at least one transition metal impregnated onto the zeolite particles. The at least one transition metal can include iron, nickel, or combinations of these, and the transition metal, following impregnation and calcination, may be present as the transition metal oxide at the surfaces of the zeolite particles.

As previously discussed, the cracking catalyst includes zeolite particles that comprise a shape selective zeolite. Shape selective zeolites can be active to catalytically crack hydrocarbon compounds, such as mixed butenes or other olefins, to produce one or more lighter olefins, such as ethylene, propylene, or both. Without being bound by any particular theory, it is believed that the shape selective zeolite may have a greater propensity to crack the relatively lighter hydrocarbons, such as mixed butenes and other olefins, compared to other types of zeolites, such as large pore zeolites. The shape selective zeolite can be an MFI structured zeolite. In embodiments, the shape selective zeolite is ZSM-5 zeolite. As used in the present disclosure, "ZSM-5" refers to zeolites having an MFI framework type according to the IUPAC zeolite nomenclature and consisting of silica and alumina. ZSM-5 refers to "Zeolite Socony Mobil-5" and is a pentasil family zeolite that can be represented by the chemical formula $Na_nAl_nSi_{96-n}O_{192} \cdot 16H_2O$, where $0<n<27$.

The ZSM-5 zeolite may have a high molar ratio of silica ($SiO_2$) to alumina ($Al_2O_3$). The ZSM-5 zeolite can have a molar ratio of silica to alumina that is greater than or equal to 500, greater than or equal to 800, greater than or equal to 1000, or even greater than or equal to 1100. The greater molar ratio of silica to alumina may reduce the intensity of the cracking reactions, which may result in reduced formation of side products from the cracking reactions. When the silica to alumina ratio is less than about 500, the acidity of the cracking catalyst may be too great, resulting in increased cracking intensity and formation of side products, resulting in decreased yield of propylene, ethylene, or both. In embodiments, the ZSM-5 zeolite has a molar ratio of silica to alumina of from 500 to 2000, such as from 500 to 1500, from 500 to 1200, from 800 to 2000, from 800 to 1500, from 800 to 1200, from 1000 to 2000, from 1000, to 1500, from 1000 to 1200, from 1100 to 2000, from 1100 to 1500, from 1100 to 1200, or about 1152.

In embodiments, the ZSM-5 zeolite may have an average surface area from 200 meters squared per gram (m$^2$/g) to 800 m$^2$/g. In embodiments, the average surface area may be from 200 m$^2$/g to 400 m$^2$/g, from 200 m$^2$/g to 600 m$^2$/g, from 200 m$^2$/g to 800 m$^2$/g, from 300 m$^2$/g to 400 m$^2$/g, from 300 m$^2$/g to 600 m$^2$/g, from 300 m$^2$/g to 800 m$^2$/g, from 400 m$^2$/g to 600 m$^2$/g, or from 400 m$^2$/g to 800 m$^2$/g. In embodiments, the ZSM-5 zeolite, can have an average total pore volume per unit weight of the ZSM-5 zeolite of from 0.010 milliliters per gram (mL/g) to 0.500 mL/g, such as from 0.050 mL/g to 0.500 mL/g, from 0.010 mL/g to 0.300 mL/g, or from 0.050 mL/g to 0.300 mL/g.

In embodiments, the zeolite particles can include up to 80 weight percent (wt. %) ZSM-5 zeolite based on the total weight of the zeolite particles. In embodiments, the zeolite particles can include from 50 wt. % to 80 wt. %, from 50 wt. % to 75 wt. %, from 50 wt. % to 70 wt. %, from 50 wt. % to 69.9 wt. %, 50 wt. % to 65 wt. %, from 50 wt. % to 60 wt. %, from 60 wt. % to 80 wt. %, from 60 wt. % to 75 wt. %, 60 wt. % to 70 wt. %, from 60 wt. % to 69.9 wt. %, from 60 wt. % to 65 wt. %, from 65 wt. % to 80 wt. %, from 65 wt. % to 75 wt. %, from 65 wt. % to 70 wt. %, from 65 wt. % to 69.9 wt. %, from 70 wt. % to 80 wt. %, from 70 wt. % to 75 wt. %, or from 75 wt. % to 80 wt. % of the ZSM-5 zeolite based on the total weight of the zeolite particles. In embodiments, the cracking catalyst can include from 50 wt. % to 80 wt. % of the ZSM-5 zeolite based on the total weight of the cracking catalyst. In embodiments, the cracking catalyst can include from 50 wt. % to 75 wt. %, from 50 wt. % to 70 wt. %, from 50 wt. % to 69.9 wt. %, 50 wt. % to 65 wt. %, from 50 wt. % to 60 wt. %, from 60 wt. % to 80 wt. %, from 60 wt. % to 75 wt. %, 60 wt. % to 70 wt. %, from 60 wt. % to 69.9 wt. %, from 60 wt. % to 65 wt. %, from 65 wt. % to 80 wt. %, from 65 wt. % to 75 wt. %, from 65 wt. % to 70 wt. %, from 65 wt. % to 69.9 wt. %, from 70 wt. % to 80 wt. %, from 70 wt. % to 75 wt. %, or from 75 wt. % to 80 wt. % of the ZSM-5 zeolite based on the total weight of the cracking catalyst.

As previously discussed, the zeolite particles comprise a binder or matrix material. A refractory binder or matrix material can be utilized to facilitate fabrication of the zeolite particles, to provide strength to the cracking catalyst, and to reduce fabrication costs. Suitable binders include inorganic oxides, such as one or more of alumina, magnesia, zirconia, chromia, titania, boric, phosphate, zinc oxide, silica, or combinations of these. In embodiments, the binder is an alumina-based binder. One commercial embodiment of an alumina binder is Cataloid AP-3, obtained from Catalysts & Chemicals Industries Co., Ltd (CCIC), Japan. Other alumina binders can also be used. In embodiments, the zeolite particles can include from greater than or equal to 19 wt. %, greater than or equal to 20 wt. %, greater than or equal to 29 wt. %, or greater than or equal to 30 wt. % alumina binder based on the total weight of the zeolite particles. The zeolite particles can include less than or equal to 50 wt. %, less than or equal to 49 wt. %, less than or equal to 45 wt. %, less than or equal to 40 wt. %, less than or equal to 39 wt. %, less than or equal to 35 wt. %, or less than or equal to 30 wt. % alumina binder based on the total weight of the zeolite particles. In embodiments, the zeolite particles can include 19 wt. % to 50 wt. %, from 20 wt. % to 50 wt. %, from 20 wt. % to 45 wt. %, from 20 wt. % to 40 wt. %, from 20 wt. % to 35 wt. %, from 20 wt. % to 30 wt. %, from 25 wt. % to 50 wt. %, from 25 wt. % to 45 wt. %, from 25 wt. % to 40 wt. %, from 25 wt. % to 35 wt. %, from 25 wt. % to 30 wt. %, from 30 wt. % to 50 wt. %, from 30 wt. % to 45 wt. %, from 30 wt. % to 40 wt. %, or from 30 wt. % to 35 wt. % alumina binder based on the total weight of the zeolite particles.

The ratio by weight of shape selective zeolite to alumina binder in the cracking catalyst can be around 4 to 1 (80 wt. % shape selective zeolite and 20 wt. % alumina binder), around 3 to 1 (75 wt. % shape selective zeolite and 25 wt. % alumina binder), or 2 to 1 (67 wt. % shape selective zeolite and 33 wt. % alumina binder). In embodiments, the zeolite particles can comprise 70 wt. % shape selective zeolite and 30 wt. % alumina binder based on the total weight of the zeolite particles.

The zeolite particles can be formed by preparing a mixture comprising the shape selective zeolite, the alumina binder, a peptizing agent, and water and extruding the mixture to produce the zeolite particles. The zeolite particles may then be dried to remove the majority of the water from the zeolite particles. The shape selective zeolite in dry powdered form may be mixed with the alumina binder in aqueous form to yield a homogeneous mixture, thus ensuring homogeneous composition of the extrudates formed. A peptizing agent may be added to the mixture prior to extruding. In embodiments, the peptizing agent can be a phosphorous-containing peptizing agent, such as but not limited to phosphoric acid. In embodiments, the zeolite particles are extruded in the presence of the alumina binder and phosphoric acid as the peptizing agent. The zeolite particles can be extruded at a temperature of from 100° C. to 150° C.

Following extrusion, the zeolite particles can have a minimal amount of phosphorous. In embodiments, the zeolite particles can have a phosphorous content of less than or equal to 1000 parts per million by weight (ppmw) based on the total weight of the zeolite particles. In embodiments, the zeolite particles comprise less than or equal to 500 ppmw, less than or equal to 200 ppmw, less than or equal to 100 ppmw, or even less than or equal to 50 ppmw phosphorous based on the total weight of the zeolite particles. In embodiments, the zeolite particles can include greater than 0 (zero) ppmw and less than or equal to 1000 ppmw phosphorous based on the total weight of the zeolite particles. In embodiments, the zeolite particles can include from 0.1 ppmw to 1000 ppmw phosphorous, such as from 0.1 ppmw to 500 ppmw, from 0.1 ppmw to 200 ppmw, from 0.1 ppmw to 100 ppmw, or from 0.1 ppmw to 50 ppmw phosphorous based on the total weight of the zeolite particles. The presence of some phosphorous in the zeolite particles can help in stabilizing the structure of the zeolite particles and can preserve the crystallinity of the zeolite particle, leading to enhanced performance. However, when the phosphorous content is too high, such as greater than 1000 ppmw, the phosphorous may decrease the acidity of the zeolite particles, which can result in decreasing the catalytic activity of the zeolite particles.

Following formation of the zeolite particles, the zeolite particles are then impregnated with the one or more transition metals compounds. The zeolite particles can be impregnated by adding the zeolite particles to a solution of one or more transition metal compound precursors in water, mixing, and then drying the resulting impregnated zeolite particles to remove the water. In embodiments, the transition metal compound precursors can be a transition metal salts, such as but not limited to a transition metal nitrate salt or other salt comprising the transition metal. The cracking catalyst of the present disclosure is not particularly limited by the type of transition metal compound precursor utilized in the wet impregnation process. In embodiments, the transition metal can be any metal from groups 6-10 of the International Union of Pure and Applied Chemistry (IUPAC) periodic table of elements. In embodiments, the transition metal can be iron, nickel, or a combination of both. After drying, the impregnated zeolite particles can be calcined to produce the cracking catalyst. In embodiments, the impregnated zeolite particles can be calcined under air at a calcination temperature of from 450° C. to 600° C. for a calcination period of from 4 hours to 8 hours. Drying and calcination can convert the transition metal compound precursor to the transition metal oxide.

The result of the process is the cracking catalyst comprising at least one transition metal oxide impregnated onto the zeolite particles. In embodiments, the at least one transition metal oxide is selected from the group consisting of iron oxide, nickel oxide, or iron oxide and nickel oxide. In embodiments, the cracking catalyst can include iron oxide in an amount sufficient to increase the yield of propylene and ethylene from catalytic cracking of mixed butenes compared to the zeolite particles without the iron oxide. In embodiments, the cracking catalyst can include from 0.14 wt. % to 0.56 wt. % iron oxide based on the total weight of the cracking catalyst. In embodiments, the cracking catalyst can include from 0.14 wt. % to 0.5 wt. %, from 0.14 wt. % to 0.48 wt. %, from 0.14 wt. % to 0.45 wt. %, from 0.14 wt. % to 0.4 wt. %, from 0.2 wt. % to 0.56 wt. %, from 0.2 wt. % to 0.5 wt. %, from 0.2 wt. % to 0.48 wt. %, from 0.2 wt. % to 0.45 wt. %, or from 0.2 wt. % to 0.4 wt. % iron oxide based on the total weight of the cracking catalyst. In embodiments, the cracking catalyst can include less than 0.56 wt. %, less than 0.50 wt. %, less than or equal to 0.48 wt. %, less than or equal to 0.45 wt. %, or even less than or equal to 0.40 wt. % iron oxide based on the total weight of the cracking catalyst. In embodiments, the cracking catalyst can comprise from 0.1 wt. % to 0.4 wt. % iron atoms based on the weight of iron atoms (without the oxygen) and the total weight of the cracking catalyst.

Alternatively or additionally, in embodiments, the cracking catalyst can comprise nickel oxide in an amount sufficient to increase the yield of propylene and ethylene from catalytic cracking of mixed butenes compared to the zeolite particles without the nickel oxide. In embodiments, the cracking catalyst can include from 0.13 wt. % to 0.52 wt. % nickel oxide based on the total weight of the cracking catalyst. In embodiments, the cracking catalyst can include from 0.13 wt. % to 0.5 wt. %, from 0.13 wt. % to 0.48 wt. %, from 0.13 wt. % to 0.45 wt. %, from 0.13 wt. % to 0.4 wt. %, from 0.2 wt. % to 0.52 wt. %, from 0.2 wt. % to 0.5 wt. %, from 0.2 wt. % to 0.48 wt. %, from 0.2 wt. % to 0.45 wt. %, or from 0.2 wt. % to 0.4 wt. % nickel oxide based on the total weight of the cracking catalyst. In embodiments, the cracking catalyst can include less than 0.52 wt. %, less than 0.50 wt. %, less than or equal to 0.48 wt. %, less than or equal to 0.45 wt. %, or even less than or equal to 0.40 wt. % nickel oxide based on the total weight of the cracking catalyst. In embodiments, the cracking catalyst can comprise from 0.1 wt. % to 0.4 wt. % nickel atoms based on the weight of nickel atoms (without the oxygen) and the total weight of the cracking catalyst.

In embodiments, the cracking catalyst can include both iron oxide and nickel oxide. In embodiments, the cracking catalyst can include from 0.14 wt. % to 0.56 wt. % or from 0.14 wt. % to less than 0.5 wt. % iron oxide based on the total weight of the cracking catalyst and from 0.13 wt. % to 0.52 wt. % or from 0.13 wt. % to less than 0.5 wt. % nickel oxide based on the total weight of the cracking catalyst. In embodiments, the cracking catalyst can comprises from 0.1 wt. % to 0.4 wt. % iron, nickel, or both based on the weight of the metal atoms (iron atoms and nickel atoms without the oxygen) and the total weight of the cracking catalyst.

In embodiments, the cracking catalyst can include the zeolite particles comprising ZSM-5 zeolite having a silica to alumina molar ratio of from 500 to 2000, or from 1100 to 1200, and about 30 wt. % alumina binder based on the total weight of the cracking catalyst. The cracking catalyst can further include from 0.14 wt. % to 0.56 wt. % iron oxide based on the total weight of the cracking catalyst, from 0 wt. % to 0.52 wt. % nickel oxide based on the total weight of the cracking catalyst, and less than or equal to 1000 ppmw phosphorous based on the total weight of the cracking catalyst. In embodiments, the cracking catalyst can further comprise less than 500 ppmw, less than 200 ppmw, less than 100 ppmw, or even less than 50 ppmw phosphorous based on the total weight of the cracking catalyst. In embodiments, the cracking catalyst consists of or consists essentially of ZSM-5 zeolite having a silica to alumina molar ratio of from 500 to 2000, an alumina binder, from 0.14 wt. % to 0.56 wt. % iron oxide based on the total weight of the cracking catalyst, from 0 wt. % to 0.52 wt. % nickel oxide based on the total weight of the cracking catalyst, and less than or equal to 1000 ppmw phosphorous based on the total weight of the cracking catalyst.

The cracking catalyst can be in the form of shaped particles, such as generally spherical catalyst particles. In embodiments, the cracking catalyst can have a particle size of from 212 micrometers to 300 micrometers. The size of the catalyst particles refers to the maximum length of a particle from one side to another, measured along the longest distance of the catalyst particle. For instance, a spherically shaped catalyst particle has a size equal to its diameter, or a rectangular prism shaped catalyst particle has a maximum length equal to the hypotenuse stretching from opposite corners. Following preparation of the cracking catalyst, in embodiments, the cracking catalyst can be sieved to produce cracking catalyst having particle size of from 212 micrometers to 300 micrometers. Thus, the cracking catalyst can include particles that pass through a 300 micrometer screen but do not pass through a 212 micrometer screen. In embodiments, the cracking catalyst can have an average particle size of from 40 micrometers (μm) to 600 μm, such as from 40 μm to 500 μm, from 40 μm to 400 μm, from 40 μm to 300 μm, from 100 μm to 600 μm, from 100 μm to 500 μm, from 100 μm to 400 μm, from 100 μm to 300 μm, from 200 μm to 600 μm, from 200 μm to 500 μm, from 200 μm to 400 μm, from 200 μm to 300 μm, or from 212 μm to 300 μm.

As previously discussed, the cracking catalyst of the present disclosure can be used in a process for catalytically cracking mixed butenes and other olefins to produce propylene, ethylene, or both. As previously discussed, the process for catalytically cracking olefins to produce propylene, ethylene, or both can include providing a feed stream comprising at least mixed butenes and then contacting the feed stream with the cracking catalyst of the present disclosure under reaction conditions sufficient to catalytically crack at least a portion of the mixed butenes or other olefins in the feed stream to produce propylene, ethylene, or both.

The feed stream can comprise one or more olefins, such as mixed butenes, mixed pentenes, mixed hexenes, or other olefins. The feed stream can comprise at least mixed butenes, such as but not limited to 1-butene, cis-2-butene, trans-2-butene, isobutene, or combinations of these. In embodiments, the feed stream can be a C4 stream, which can include mixed butenes as well as other C4 compounds, such as but not limited to butane, isobutane, 1,3-butadiene, or combinations of these. In embodiments, the feed stream can be a C4 stream recovered from a steam cracking process or a fluidized catalytic cracking process. In embodiments, the feed stream can comprise, consist of, or consist essentially of 1-butene, 2-butenes, isobutane, and n-butane, where the 2-butenes comprise cis-2-butene, trans-2-butene, or both.

In embodiments, the feed stream can comprise 1-butene. In embodiments, the feed stream can comprise from 12.5 wt. % to 50 wt. % 1-butene based on the total mass flow rate of the feed stream. In embodiments, the feed stream can comprise from 12.5 wt. % to 45 wt. %, from 12.5 wt. % to 40 wt. %, from 20 wt. % to 50 wt. %, from 20 wt. % to 45 wt. %, from 20 wt. % to 40 wt. %, from 25 wt. % to 50 wt. %, from 25 wt. % to 45 wt. %, from 25 wt. % to 40 wt. %, from 30 wt. % to 50 wt. %, from 30 wt. % to 45 wt. %, from 30 wt. % to 40 wt. %, or from 40 wt. % to 50 wt. % 1-butene based on the total mass flow rate of the feed stream. In embodiments, the feed stream can comprise 2-butenes, including cis-2-butene, trans-2-butene, or both. In embodiments, the feed stream can comprise from 12.5 wt. % to 30 wt. % 2-butenes based on the total mass flow rate of the feed stream. In embodiments, the feed stream can comprise from 12.5 wt. % to 25 wt. %, from 12.5 wt. % to 20 wt. %, from 12.5 wt. % to 15 wt. %, from 15 wt. % to 30 wt. %, from 15 wt. % to 25 wt. %, from 15 wt. % to 20 wt. %, from 20 wt. % to 30 wt. %, or from 20 wt. % to 25 wt. % 2-butenes based on the total mass flow rate of the feed stream.

In embodiments, the feed stream can comprise isobutane. In embodiments, the feed stream can comprise from 15 wt. % to 30 wt. % isobutane based on the total mass flow rate of the feed stream. In embodiments, the feed stream can comprise from 15 wt. % to 25 wt. %, from 15 wt. % to 20 wt. %, from 15 wt. % to 30 wt. %, from 15 wt. % to 25 wt. %, from 15 wt. % to 20 wt. %, from 20 wt. % to 30 wt. %, or from 20 wt. % to 25 wt. % isobutane based on the total mass flow rate of the feed stream. In embodiments, the feed stream can comprise n-butane. In embodiments, the feed stream can comprise from 5 wt. % to 55 wt. % n-butane based on the total mass flow rate of the feed stream. In embodiments, the feed stream can comprise from 5 wt. % to 50 wt. %, from 5 wt. % to 45 wt. %, from 5 wt. % to 40 wt. %, from 5 wt. % to 30 wt. %, from 5 wt. % to 10 wt. %, from 10 wt. % to 55 wt. %, from 10 wt. % to 50 wt. %, from 10 wt. % to 45 wt. %, from 10 wt. % to 40 wt. %, from 20 wt. % to 55 wt. %, from 20 wt. % to 50 wt. %, from 20 wt. % to 45 wt. %, from 20 wt. % to 40 wt. %, from 30 wt. % to 55 wt. %, from 30 wt. % to 50 wt. %, from 30 wt. % to 45 wt. %, from 30 wt. % to 40 wt. %, or from 40 wt. % to 55 wt. % n-butane based on the total mass flow rate of the feed stream. The feed stream can also include other C4 constituents, such as but not limited to isobutene, 1,3-butadiene, or other C4 compounds. If present, the 1,3-butadiene concentration in the feed stream can be less than or equal to 0.1 wt. % 1,3-butadiene based on the total mass flow rate of the feed stream.

In embodiments, the feed stream to the catalytic cracking process can be an effluent from a metathesis reactor for converting mixed butenes to propylene, ethylene, or both through one or more metathesis reactions. When the feed stream is an effluent from a metathesis reactor, the feed stream can further include greater molecular weight olefins, such as mixed pentenes, mixed hexenes, or other greater molecular weight olefins resulting from metathesis of mixed butenes. The feed stream can also include propylene, ethylene, or both produced from the metathesis reactions. When the feed stream is an effluent from a metathesis reactor, the feed stream can also include other reaction products resulting from the metathesis reactions.

The feed stream generally does not include nitrogen or air. Without intending to be bound by any particular theory, it is believed that the presence of nitrogen, air, or both can cause side reactions in the cracking reactor resulting in reduced yield of propylene, ethylene, or both. In embodiment, the feed stream is substantially free of nitrogen, air, or both, such as having less than 0.1 wt. % or even less than 0.01 wt. % nitrogen, air, or both based on the total mass flow rate of the feed stream.

Figure 1:
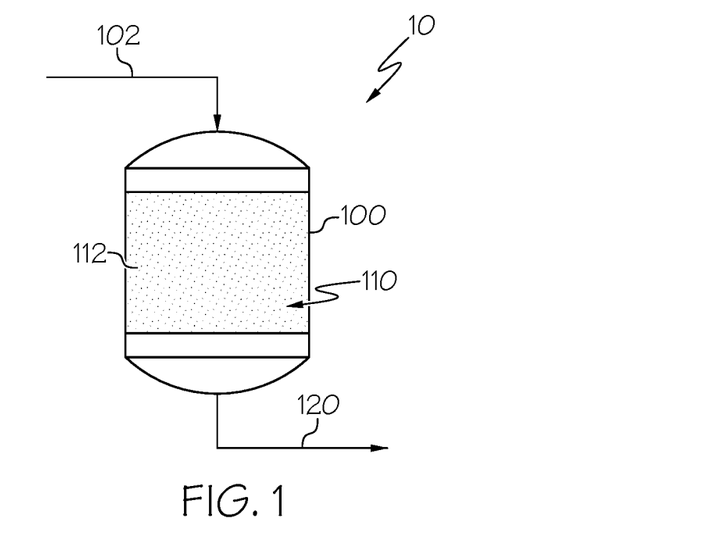
FIG. 1 schematically depicts a generalized flow diagram of a fixed bed reactor system for converting mixed butenes to propylene, ethylene, or both through catalytic cracking, according to one or more embodiments shown and described in the present disclosure.

Referring now to FIG. 1, a reactor system 10 comprising a cracking reactor 100 for converting the feed stream 102 comprising at least mixed butenes to propylene, ethylene, or both is schematically depicted. The feed stream 102 is passed to the cracking reactor 100, which comprises at least a cracking reaction zone 110 comprising the cracking catalyst 112. In embodiments, the cracking reactor 100 can be a fixed bed reactor. Other types of reactors, such as but not limited to moving bed reactors, fluidized bed reactors, and the like can also be used to for the cracking reactor 100. Although shown as a downflow reactor in FIG. 1, the cracking reactor 100 can also be an upflow reactor, a horizontal flow reactor, or have any other suitable flow pattern suitable for contacting the feed stream 102 with the cracking catalyst 112.

In the cracking reactor 100, the feed stream 102 comprising the mixed butenes can be contacted with the cracking catalyst 112 at reaction conditions sufficient to cause catalytic cracking of at least a portion of the mixed butenes or other olefins in the feed stream 102 to produce a cracking effluent 120 comprising propylene, ethylene, or both. Contact of the mixed butenes or other olefins in the feed stream 102 with the cracking catalyst 112 at the reaction conditions can cause at least a portion of the mixed butenes or other olefins to undergo cracking reactions to convert the olefins into propylene, ethylene, or both. The feed stream 102 can be contacted with the cracking catalyst 112 in the cracking reaction zone 110 at a temperature sufficient to cause cracking of the olefins to produce the cracking effluent 120 comprising propylene, ethylene, or both. In embodiments, the process can include contacting the feed stream 102 with the cracking catalyst 112 at a temperature of from 300° C. to 650° C., such as from 300° C. to 600° C., from 300° C. to 550° C., from 300° C. to 500° C., from 350° C. to 650° C., from 350° C. to 600° C., from 350° C. to 550° C., from 350° C. 500° C., from 400° C. to 650° C., from 400° C. to 600° C., from 400° C. to 550° C., from 400° C. to 500° C., from 450° C. to 600° C., from 450° C. to 550° C., or from 500° C. to 600° C. In embodiments, the feed stream 102 can be contacted with the cracking catalyst 112 in the cracking reaction zone 110 at a pressure of from 1 bar (100 kPa) to 30 bar (3,000 kPa) or from 2 bar (200 kPa) to 20 bar (2,000 kPa). In embodiments, the feed stream 102 can be contacted with the cracking catalyst 112 in the cracking reaction zone 110 at atmospheric pressure. In embodiments, the feed stream 102 can be contacted with the cracking catalyst 112 in the cracking reaction zone 110 at a weight hourly space velocity (WHSV) of from 3 per hour ($h^{-1}$) to 10,000 $h^{-1}$, such as from 3 $h^{-1}$ to 5000 $h^{-1}$, from 3 $h^{-1}$ to 2500 $h^{-1}$, from 3 $h^{-1}$ to 1000 $h^{-1}$, from 3 $h^{-1}$ to 100 $h^{-1}$, from 3 $h^{-1}$ to 12 $h^{-1}$, from 100 $h^{-1}$ to 5000 $h^{-1}$, or from 300 $h^{-1}$ to 2500 $h^{-1}$.

The cracking catalyst 112 may be activated by passing a flow of nitrogen gas through the cracking catalyst 112 at elevated temperature prior to contacting the feed stream 102 with the cracking catalyst 112 in the cracking reaction zone 110. In embodiments, the processes of the present disclosure can include, before contacting the feed stream 102 with the cracking catalyst 112, activating the cracking catalyst 112 with a flow of nitrogen gas at a temperature of from 450° C. to 650° C., or about 550° C. for a period of from 8 hours to 24 hours.

Figure 2:
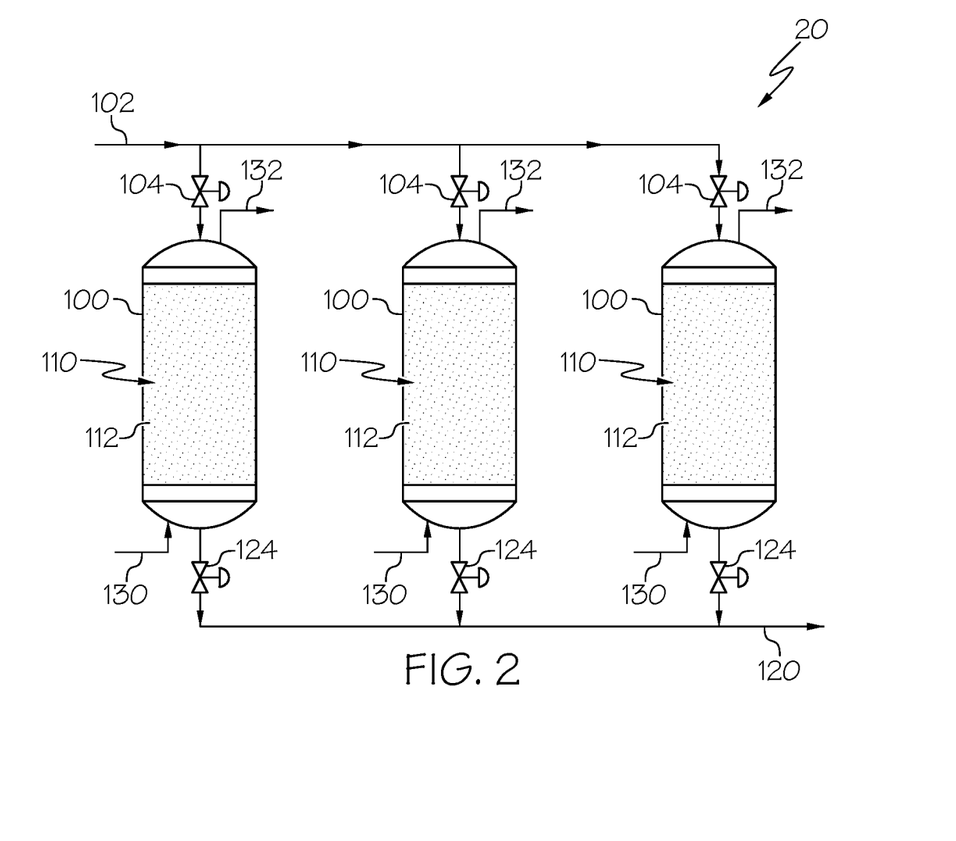
FIG. 2 schematically depicts a generalized flow diagram of a cracking reactor system comprising a plurality of fixed bed reactors for converting mixed butenes to propylene, ethylene, or both through catalytic cracking, according to one or more embodiments shown and described in the present disclosure.

Referring now to FIG. 2, in embodiments, a reactor system 20 for converting mixed butenes and other olefins to propylene and ethylene can include a plurality of reactors 100 that can be operated in parallel. Although shown in FIG. 2 as having three reactors 100, the reactor system 20 having a plurality of reactors 100 can have 2, 3, 4, 5, 6, 7, 8, or more than 8 reactors 100 operated in parallel. Each of the plurality of reactors 100 can include an inlet valve 104 that can be operable to control the flow of the feed stream 102 to each of the plurality of reactors 100. Each of the plurality of reactors 100 can also include an outlet valve 124 that can be operable to control the flow of the cracking effluent 120 from each of the reactors 100. Each cracking reactor 100 can also, optionally, include a regenerating fluid inlet 130 and a regenerating fluid outlet 132, which can be used during regeneration of the cracking catalyst 112. As shown in FIG. 2, the regenerating fluid inlet 130 and regenerating fluid outlet 132 are arranged to produce a flow of regenerating fluid counter to the flow of the reactants through the cracking reaction zone 110. However, it is understood that the regenerating fluid inlet 130 and regenerating fluid outlet 132 could be configured to direct a regenerating fluid in the same direction as the reactants flow through the cracking reaction zone 110.

The reactor system 20 can be operated in a swing mode where the feed stream 102 can be passed to a first subset of the reactors 100 of the system 20 while a second subset of the reactors 100 of the system 20 are subjected to regeneration or reconditioning of the cracking catalyst 112 or replacement of the cracking catalyst 112. The feed stream 102 can be passed to the first subset of reactors 100 until the composition of the cracking effluent 120 indicates that the cracking catalyst 112 in the cracking reaction zone 110 of the first subset of reactors 100 is due for regeneration. Regeneration, reconditioning, or replacement of the cracking catalyst 112 is indicated when the activity of the cracking catalyst 112 has decreased, resulting in an unacceptable decrease in yield of propylene and ethylene in the cracking effluent 120. When the cracking effluent 120 indicates reduced catalytic activity, the feed stream 102 can be diverted to the second subset of reactors 100 by changing the positions of the inlet valves 104 and the outlet valves 124 for the reactors in the first subset and second subset of the reactors 100. Then, the feed stream 102 can be contacted with cracking catalyst 112—which has been regenerated, reconditioned, or replaced—in the second subset of reactors 100 while the used cracking catalyst 112 in the first subset of reactors 100 is being regenerated, reconditioned, or replaced.

Figure 3:
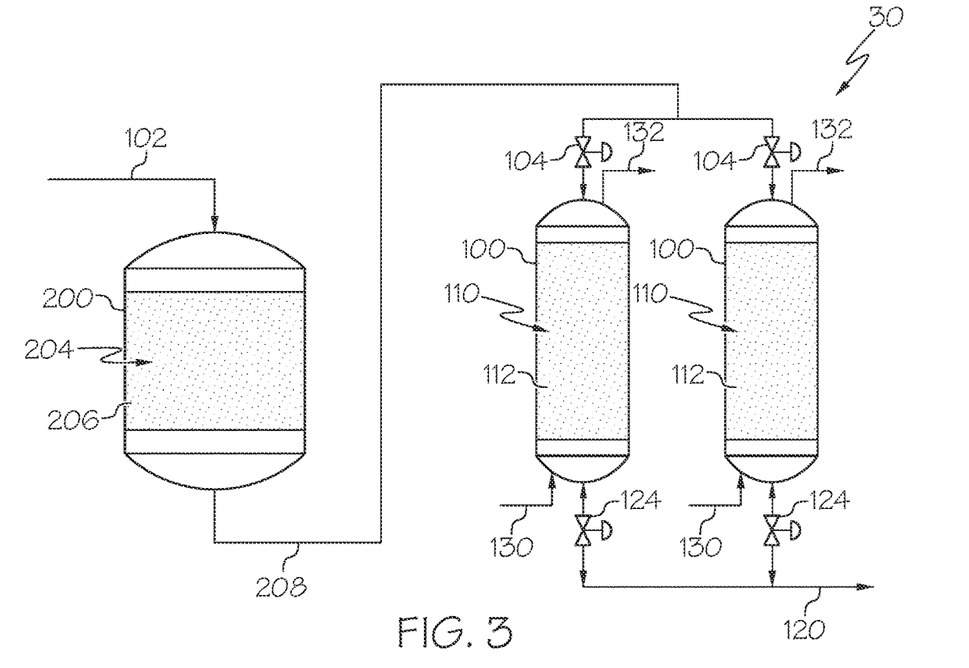
FIG. 3 schematically depicts a generalized flow diagram of a system for converting mixed butenes to propylene, ethylene, or both through metathesis and catalytic cracking, according to one or more embodiments shown and described in the present disclosure.

Referring now to FIG. 3, in embodiments, the cracking catalyst can be used in a dual metathesis and cracking system 30 for converting mixed butenes to propylene, ethylene, or both through a combination of metathesis and cracking. The dual metathesis and cracking system 30 can include a metathesis reactor 200 comprising a metathesis reaction zone 204 that includes a metathesis catalyst 206, such as but not limited to a tungsten or tungsten oxide catalyst supported on a silica, alumina, or a silica-alumina support. The dual metathesis and cracking system 30 can further include at least one cracking reactor 100 disposed downstream of the metathesis reactor 200. In the dual metathesis and cracking system 30 of FIG. 3, the feed stream 102 is passed to the metathesis reactor 200, where the feed stream 102 is contacted with the metathesis catalyst 206 in the metathesis reaction zone 204 at metathesis reaction conditions. Contact of the feed stream 102 with the metathesis catalyst 206 at metathesis reaction conditions can cause at least a portion of the mixed butenes to undergo metathesis reactions to produce other olefins, such as but not limited to propylene, ethylene, pentene, hexene, or combinations of these. The metathesis reaction conditions can be similar to the cracking reaction conditions previously discussed. In embodiments, the feed stream 102 can be contacted with the metathesis catalyst 206 at a temperature of from 300° C. to 650° C., a pressure of from 1 bar (100 kPa) to 30 bar (3,000 kPa), and a weight hourly space velocity (WHSV) of from 3 per hour ($h^{-1}$) to 10,000 $h^{-1}$. The metathesis effluent 208 can be passed out of the metathesis reactor 200. The metathesis effluent 208 can include propylene, ethylene, unreacted mixed butenes, mixed pentenes, mixed hexenes, butane, isobutane, or combinations of these.

The metathesis effluent 208 can be passed from the metathesis reactor 200 to the cracking reactor 100, where the metathesis effluent 208 is contacted with the cracking catalyst 112 in the cracking reaction zone 110. In embodiments, the metathesis effluent 208 can be passed directly from the metathesis reactor 200 to the cracking reactor 100 without separation or any other intervening unit operation. The cracking reaction conditions can be any of the reaction conditions previously discussed for the cracking reactor 100. Contacting the metathesis effluent 208 with the cracking catalyst 112 in the cracking reaction zone 110 can cause cracking reactions that can convert, mixed pentenes, mixed hexenes, unreacted mixed butenes or combinations of these to produce additional propylene, ethylene, or both. Thus, the cracking effluent 120 passed out of the cracking reactors 100 can have a greater concentration and yield of propylene, ethylene, or both compared to the metathesis effluent 208.

Figure 4:
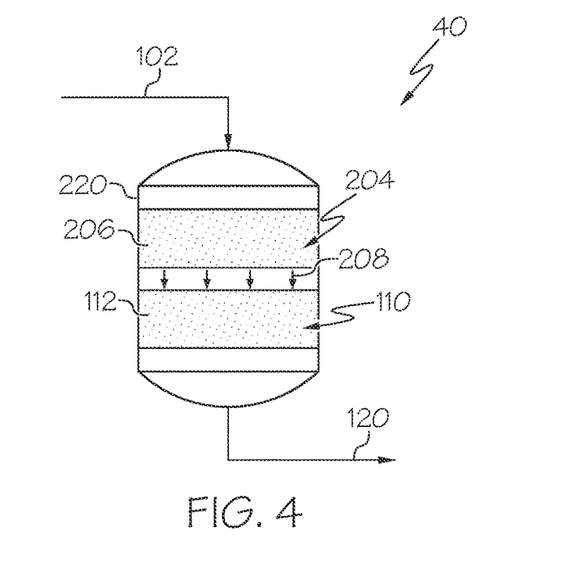
FIG. 4 schematically depicts a generalized flow diagram of a another system for converting mixed butenes to propylene, ethylene, or both through metathesis and catalytic cracking, according to one or more embodiments shown and described in the present disclosure.

Referring now to FIG. 4, in embodiments, the cracking catalyst 112 of the present disclosure can be incorporated into a dual metathesis and cracking system 40 that comprises a combined metathesis and cracking reactor 220 that includes a metathesis reaction zone 204 and a cracking reaction zone 110 disposed in the same metathesis and cracking reactor 220. The cracking reaction zone 110 comprising the cracking catalyst 112 can be disposed downstream of the metathesis reaction zone 204 comprising the metathesis catalyst 206. The metathesis effluent 208 can pass directly from the metathesis reaction zone 204 to the cracking reaction zone 110. The combined metathesis and cracking reactor 220 can be operated at any of the operating conditions previously discussed.

Figure 5:
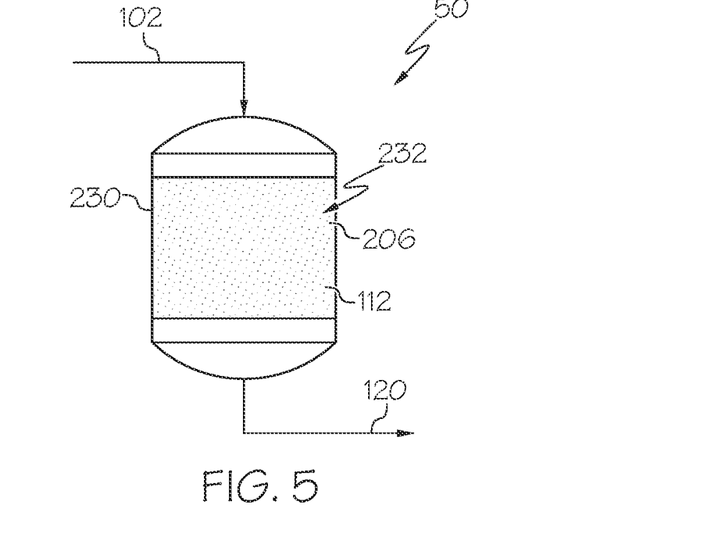
FIG. 5 schematically depicts a generalized flow diagram of still another system for converting mixed butenes to propylene, ethylene, or both through metathesis and catalytic cracking, according to one or more embodiments shown and described in the present disclosure.

Referring now to FIG. 5, in some embodiments, the cracking catalyst 112 of the present disclosure can be incorporated into a metathesis and cracking system 50 in which the cracking catalyst 112 is combined and mixed with the metathesis catalyst 206 in a combined reaction zone 232 in a combined metathesis and cracking reactor 230.

EXAMPLES

The various aspects of the present disclosure will be further clarified by the following examples. The examples are illustrative in nature and should not be understood to limit the subject matter of the present disclosure.

Examples 1-15: Preparation of Cracking Catalyst

In Examples 1-15, cracking catalysts comprising ZSM-5 and transition metal oxide impregnated onto the catalyst particles were prepared. The ZSM-5 zeolite has a silica to alumina molar ratio of 1152. Each cracking catalyst was prepared by first extruding 4 grams of the zeolite particles using a mixture of the ZSM-5 zeolite, an alumina binder, and phosphoric acid peptizer. Following extrusion, each of the transition metal oxides were impregnated onto the zeolite particles by dissolving the transition metal nitrates in 3.5 milliliters (mL) of deionized water. Iron (Fe) was impregnated using iron nitrate salt dissolved in the deionized water, and nickel was impregnated using nickel nitrate salt dissolved in deionized water. The 4 grams of the zeolite particles comprising the ZSM-5 and peptized alumina binder were added to the metal nitrate solution and the catalysts were allowed to dry at room temperature for 3 hours. The cracking catalysts were then calcined at 550° C. with a ramping rate of 0.5° C. per minute under air. Calcining in the presence of air converted the transition metal nitrates to transition metal oxides. The metal loading for each of the cracking catalysts of Examples 1-15 are provided in Table 1. Although present in the cracking catalyst as metal oxides, the metal loading in Table 1 is provided as weight percentage of elemental transition metal based on the total weight of the cracking catalyst (oxygen not included in wt. %).

TABLE 1

| Example | Iron Amount (wt. % metal) | Nickel Amount (wt. % metal) |
|---|---|---|
| 1 | 0.1 | — |
| 2 | 0.2 | — |
| 3 | 0.4 | — |
| 4 | — | 0.1 |
| 5 | — | 0.2 |
| 6 | — | 0.4 |
| 7 | 0.1 | 0.1 |
| 8 | 0.1 | 0.2 |
| 9 | 0.1 | 0.4 |
| 10 | 0.2 | 0.1 |
| 11 | 0.2 | 0.2 |
| 12 | 0.2 | 0.4 |
| 13 | 0.4 | 0.1 |
| 14 | 0.4 | 0.2 |
| 15 | 0.4 | 0.4 |
| Comparative Example 16 | — | — |

Comparative Example 16: Zeolite Particles with No Transition Metal

For Comparative Example 16, zeolite particles were prepared by extruding a mixture comprising the ZSM-5 with the alumina binder and phosphoric acid peptizer as discussed in Examples 1-15. The ZSM-5 had a silica to alumina molar ratio of 1152, which was the same as in Examples 1-15. The type and amount of alumina binder and phosphoric acid peptizer were the same as in Examples 1-15. For Comparative Example 16, no transition metals were impregnated onto the zeolite particles. Instead, the zeolite particles of Comparative Example 16 were calcined under the same conditions discussed in Examples 1-15.

Example 17: Cracking Catalyst Evaluation

In Example 17, the cracking catalysts of Examples 1-15 and Comparative Example 16 were evaluated by conducting catalyst performance tests using a high-throughput screen reactor system manufactured by the HTE Company. The screen reactor system included 16 individual reactors that are grouped together and isothermally heated so that all the cracking catalysts are tested at the same reaction temperature of 550° C. The cracking catalysts were pressed and then sieved to a particle size of from 210 micrometers to 300 micrometers.

Figure 6:
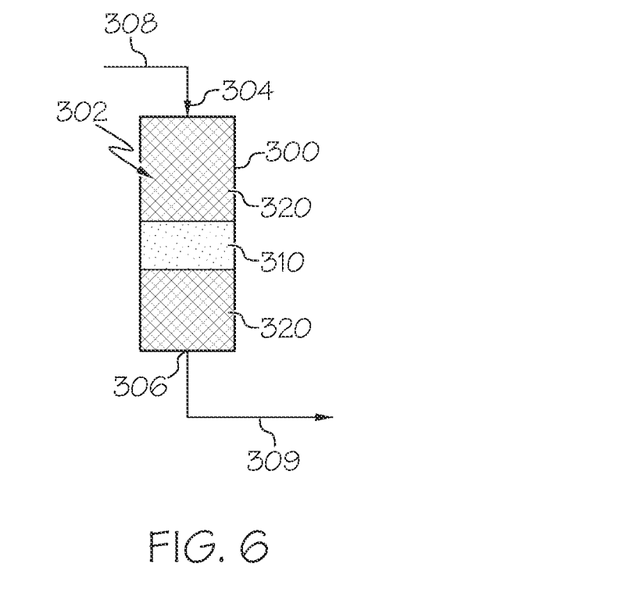
FIG. 6 schematically depicts one reactor compartment of a screening reactor system for evaluating the catalysts of the examples, according to one or more embodiments shown and described in the present disclosure.

Referring now to FIG. 6, one reactor 300 of the screen reactor system for conducting the cracking catalyst evaluation is schematically depicted. Each reactor 300 includes a reaction chamber 302 having an inlet 304 and an outlet 306. The cracking catalyst 310 is placed in the reaction chamber 302 between two layers of silicon carbide 320. For a weight hourly space velocity of 7, the amount of cracking catalyst 310 for each evaluation was 0.14 grams. The reactor temperature was monitored by thermocouple 330 placed at three difference locations to ensure isothermal heating across the reactors 300.

To conduct the evaluation, the reactor was heated to a temperature of 120° C. and maintained at that temperature under a flow of nitrogen and argon for a period of 24 hours to ensure slow moisture desorption from catalysts. The flowrate of argon was 6 mL/min and the flowrate of the nitrogen was 120 mL/min. The inlet and outlet were monitored to ensure no gas leakage from the system.

The cracking catalysts were then activated under a nitrogen flow of 120 mL/min, a temperature of 550° C. and for an activation period of 24 hours. Then, the nitrogen was turned off and a feed stream comprising mixed butenes was fed to the reactor for a period of a few days. The composition of the feed stream comprising mixed butenes is provided in Table 2. The same feed stream was used for all 16 cracking catalysts. The flow rate of the feed stream to each reactor of the screen reactor system was 0.267 grams per minute (g/min).

TABLE 2

| Constituent of the Feed Stream | Weight Percent |
|---|---|
| 2-butene | 45 |
| cis-2-butene | 12.5 |
| trans-2-butene | 12.5 |
| iso-butane | 20 |
| n-butane | 10 |

The flow rate of the feed stream to each reactor of the screen reactor system was 0.267 grams per minute (g/min). An Agilent 7890B online gas chromatographer with helium as a carrier gas was used to analyze the products with a thermal conductivity detector (TCD) for light gases and two flame ionization detectors (FID) to identify C1-C6 hydrocarbons. The total olefins yield was determined from the measured compositions. In Example 17, the total olefins yield refers to the yield of propylene and ethylene. The total olefins yield does not include the amount of unreacted butenes. The total olefin yields for each of the cracking catalysts of Examples 1-15 and Comparative Example 16 are provided in Table 3.

TABLE 3

| Cracking Catalyst | Iron (wt. % metal) | Nickel (wt. % metal) | Total Olefins Yield (%) | % Improvement |
|---|---|---|---|---|
| 1 | 0.1 | — | 42.8 | 23.3 |
| 2 | 0.2 | — | 41.8 | 20.5 |
| 3 | 0.4 | — | 40.7 | 17.3 |
| 4 | — | 0.1 | 35.5 | 2.3 |
| 5 | — | 0.2 | 34.4 | — |
| 6 | — | 0.4 | 35.1 | 1.2 |
| 7 | 0.1 | 0.1 | 40.8 | 17.6 |

TABLE 3-continued

| Cracking Catalyst | Iron (wt. % metal) | Nickel (wt. % metal) | Total Olefins Yield (%) | % Improvement |
|---|---|---|---|---|
| 8 | 0.1 | 0.2 | 35.4 | 2.0 |
| 9 | 0.1 | 0.4 | 37.8 | 8.9 |
| 10 | 0.2 | 0.1 | 33.9 | — |
| 11 | 0.2 | 0.2 | 32.9 | — |
| 12 | 0.2 | 0.4 | 37.0 | 6.6 |
| 13 | 0.4 | 0.1 | 34.7 | — |
| 14 | 0.4 | 0.2 | 35.7 | 2.9 |
| 15 | 0.4 | 0.4 | 34.7 | — |
| Comparative Example 16 | — | — | 34.7 | — |

As shown in Table 3, the cracking catalysts of examples 1-15 comprising the small amounts of iron oxide, nickel oxide, or both outperformed the cracking catalyst of Comparative Example 16, which did not include iron oxide, nickel oxide or both.

According to a first aspect of the present disclosure, a process for cracking olefins to produce propylene, ethylene, or both, includes providing a feed stream comprising mixed butenes and contacting the feed stream with a cracking catalyst at reaction conditions that may cause at least a portion of the mixed butenes in the feed stream to react to form propylene, ethylene, or both. The cracking catalyst may comprise zeolite particles comprising a shape selective zeolite and an alumina binder. The cracking catalyst may further comprise at least one transition metal oxide impregnated onto the zeolite particles. The at least one transition metal oxide may be selected from the group consisting of iron oxide, nickel oxide, and combinations of these.

A second aspect of the present disclosure may include the first aspect, where the cracking catalyst may comprise from 0.14 weight percent to 0.56 weight percent iron oxide based on the total weight of the cracking catalyst.

A third aspect of the present disclosure may include either one of the first or second aspects, where the cracking catalyst may comprise from 0.13 weight percent to 0.52 weight percent nickel oxide based on the total weight of the cracking catalyst.

A fourth aspect of the present disclosure may include any one of the first through third aspects, where the cracking catalyst may comprise from 0.1 to 0.4 weight percent iron, nickel, or both based on the total weight of the cracking catalyst.

A fifth aspect of the present disclosure may include any one of the first through fourth aspects, where the cracking catalyst may comprise from 0.14 weight percent to 0.56 weight percent iron oxide based on the total weight of the cracking catalyst; and from 0.13 weight percent to 0.52 weight percent nickel oxide based on the total weight of the cracking catalyst.

A sixth aspect of the present disclosure may include any one of the first through fifth aspects, where the cracking catalyst may comprise less than 1000 parts per million by weight phosphorous based on the total weight of the cracking catalyst.

A seventh aspect of the present disclosure may include any one of the first through sixth aspects, where the shape selective zeolite may be ZSM-5 zeolite.

An eighth aspect of the present disclosure may include the seventh aspect, where the ZSM-5 zeolite may comprise a silica to alumina molar ratio of from 500 to 2000 where the silica to alumina molar ratio is defined as the moles of silica divided by the moles of alumina.

A ninth aspect of the present disclosure may include any one of the first through eighth aspects, where the feed stream may comprise, consists of, or consist essentially of 1-butene, 2-butene, isobutane, and n-butane, where the 2-butene can comprise cis-2-butene and trans-2-butene.

A tenth aspect of the present disclosure may include any one of the first through ninth aspects, where the feed stream may comprise from 12.5 weight percent to 50 weight percent 1-butene, from 12.5 weight percent to 25 weight percent 2-butenes, and from 15 weight percent to 25 weight percent isobutane.

An eleventh aspect of the present disclosure may include the tenth aspect, comprising from 6.25 weight percent to 12.5 weight percent cis-2-butene and from 6.25 weight percent to 12.5 weight percent trans-2-butene.

A twelfth aspect of the present disclosure may include any one of the first through eleventh aspects, where the feed stream may comprise from 5 weight percent to 55 weight percent n-butane, or from 10 wt. % to 55 wt. % n-butane, or from 30 wt. % to 55 wt. % n-butane.

A thirteenth aspect of the present disclosure may include any one of the first through twelfth aspects, where the cracking catalyst may comprise 30 weight percent alumina binder based on the total weight of the cracking catalyst.

A fourteenth aspect of the present disclosure may include any one of the first through thirteenth aspects, where the zeolite particles may be extruded.

A fifteenth aspect of the present disclosure may include any one of the first through fourteenth aspects, where the zeolite particles may comprise a phosphorous peptizer.

A sixteenth aspect of the present disclosure may include the fifteenth aspect, where the phosphorous peptizer may comprises phosphoric acid.

A seventeenth aspect of the present disclosure may include any one of the first through sixteenth aspects, where the zeolite particles may have a particle size of from 40 micrometers to 600 micrometers, such as from 212 micrometers to 300 micrometers.

An eighteenth aspect of the present disclosure may include any one of the first through seventeenth aspects, comprising contacting the feed stream with the cracking catalyst at a temperature of from 300° C. to 650° C.

A nineteenth aspect of the present disclosure may include any one of the first through eighteenth aspects, further comprising, before contacting the feed stream with the cracking catalyst, activating the cracking catalyst with a flow of nitrogen gas at a temperature of from 450° C. to 650° C., or about 550° C. for a period of from 8 hours to 24 hours.

A twentieth aspect of the present disclosure may include any one of the first through nineteenth aspects, comprising contacting the feed stream with the cracking catalyst in a fixed bed reactor.

A twenty-first aspect of the present disclosure may include twentieth aspect, where the fixed bed reactor may comprise a plurality of fixed bed reactors in parallel.

A twenty-second aspect of the present disclosure may include the twenty-first aspect, further comprising operating the plurality of fixed bed reactors in swing mode, where operating in swing mode may comprise contacting the feed stream with the cracking catalyst in one of the plurality of fixed bed reactors and simultaneously regenerating, reconditioning, or replacing the cracking catalyst in another of the plurality of fixed bed reactors A twenty-third aspect of the present disclosure may include any one of the first through twenty-second aspects, further comprising, before contacting the feed stream with the cracking catalyst, contacting the feed stream with a metathesis catalyst in a metathesis reaction zone to produce a metathesis reaction product stream, and then contacting the metathesis reaction product stream with the cracking catalyst.

A twenty-fourth aspect of the present disclosure may include any one of the first through twenty-third aspects, comprising contacting the feed stream with a catalyst mixture comprising the cracking catalyst and a metathesis catalyst, where contacting with the catalyst mixture may convert mixed butenes from the feed stream to propylene, ethylene, or both through a combination of metathesis and catalytic cracking.

A twenty-fifth aspect of the present disclosure may be directed to a cracking catalyst that may comprise a plurality of zeolite particles comprising ZSM-5 zeolite and an alumina binder; and nickel oxide, iron oxide, or both impregnated onto the surfaces of the zeolite particles.

A twenty-sixth aspect of the present disclosure may include the twenty-fifth aspect, comprising from 0.14 weight percent to 0.56 weight percent iron oxide based on the total weight of the cracking catalyst.

A twenty-seventh aspect of the present disclosure may include either one of the twenty-fifth or twenty-sixth aspects, comprising from 0.13 weight percent to 0.52 weight percent nickel oxide based on the total weight of the cracking catalyst.

A twenty-eighth aspect of the present disclosure may include any one of the twenty-fifth through twenty-seventh aspects, comprising from 0.1 to 0.4 weight percent iron, nickel, or both based on the total weight of the cracking catalyst.

A twenty-ninth aspect of the present disclosure may include any one of the twenty-fifth through twenty-eighth aspects, comprising from 0.13 weight percent to 0.52 weight percent nickel oxide based on the total weight of the cracking catalyst and from 0.1 to 0.4 weight percent iron, nickel, or both based on the total weight of the cracking catalyst.

A thirtieth aspect of the present disclosure may include any one of the twenty-fifth through twenty-ninth aspects, where the ZSM-5 zeolite may comprise a silica to alumina molar ratio of from 500 to 2000 where the silica to alumina molar ratio is defined as the moles of silica divided by the moles of alumina.

A thirty-first aspect of the present disclosure may include any one of the twenty-fifth through thirtieth aspects, comprising from 20 weight percent to 50 weight percent alumina binder based on the total weight of the cracking catalyst.

A thirty-second aspect of the present disclosure may include any one of the twenty-fifth through thirty-first aspects, where the cracking catalyst may comprise less than or equal to 1000 parts per million by weight (ppmw) phosphorous, such as from 0.1 ppmw to 1000 ppmw phosphorous based on the total weight of the cracking catalyst.

A thirty-third aspect of the present disclosure may include any one of the twenty-fifth through thirty-second aspects, where the zeolite particles may have a particle size of from 40 micrometers to 600 micrometers.

A thirty-fourth aspect of the present disclosure may include any one of the twenty-fifth through thirty-third aspects, comprising 30 wt. % alumina binder based on the total weight of the cracking catalyst, from 0.14 weight percent to 0.56 weight percent iron oxide based on the total weight of the cracking catalyst, from 0 weight percent to 0.52 weight percent nickel oxide based on the total weight of the cracking catalyst, and less and 1000 parts per million by weight phosphorous based on the total weight of the cracking catalyst, where the ZSM-5 zeolite may comprise a silica to alumina molar ratio of from 500 to 2000.

A thirty-fifth aspect of the present disclosure may be directed to a method of producing the cracking catalyst any one of the twenty-fifth through thirty-fourth aspects, the method comprising combining the ZSM-5 zeolite, the alumina binder, a phosphorous-containing peptizer, and water to form a zeolite paste; extruding the zeolite paste to produce the zeolite particles; drying the zeolite particles; impregnating the iron oxide, the nickel oxide, or both onto the surfaces of the zeolite particles to produce impregnated zeolite particles; and drying and calcining the impregnated zeolite particles to produce the cracking catalyst.

A thirty-sixth aspect of the present disclosure may include the thirty-fifth aspect, further comprising sieving the cracking catalyst to a particle size range of from 40 micrometers to 600 micrometers.

It is noted that any two quantitative values assigned to a property may constitute a range of that property, and all combinations of ranges formed from all stated quantitative values of a given property are contemplated in this disclosure.

It is noted that one or more of the following claims utilize the term "where" as a transitional phrase. For the purposes of defining the present technology, it is noted that this term is introduced in the claims as an open-ended transitional phrase that is used to introduce a recitation of a series of characteristics of the structure and should be interpreted in like manner as the more commonly used open-ended preamble term "comprising."

Having described the subject matter of the present disclosure in detail and by reference to specific aspects, it is noted that the various details of such aspects should not be taken to imply that these details are essential components of the aspects. Rather, the claims appended hereto should be taken as the sole representation of the breadth of the present disclosure and the corresponding scope of the various aspects described in this disclosure. Further, it will be apparent that modifications and variations are possible without departing from the scope of the appended claims.

What is claimed is:

1. A process for cracking olefins to produce propylene, ethylene, or both, the process comprising:
   providing a feed stream comprising mixed butenes;
   contacting the feed stream with a cracking catalyst at reaction conditions that cause at least a portion of the mixed butenes in the feed stream to react to form propylene, ethylene, or both, where the cracking catalyst comprises:
   zeolite particles comprising a shape selective zeolite and an alumina binder;
   at least one transition metal oxide impregnated onto the zeolite particles, where the at least one transition metal oxide is selected from the group consisting of iron oxide, nickel oxide, and combinations of these; and
   phosphorus, wherein a phosphorus content of the cracking catalyst is greater than 0 parts per million by weight (ppmw) and less than 1000 ppmw phosphorous based on a total weight of the cracking catalyst.

2. The process of claim 1, where the cracking catalyst comprise from 0.14 weight percent to 0.56 weight percent iron oxide based on the total weight of the cracking catalyst.

3. The process of claim 1, where the cracking catalyst comprises from 0.13 weight percent to 0.52 weight percent nickel oxide based on the total weight of the cracking catalyst.

4. The process of claim 1, where the cracking catalyst comprises from 0.1 to 0.4 weight percent iron, nickel, or both based on the total weight of the cracking catalyst.

5. The process of claim 1, where the cracking catalyst comprises:
   from 0.14 weight percent to 0.56 weight percent iron oxide based on the total weight of the cracking catalyst; and
   from 0.13 weight percent to 0.52 weight percent nickel oxide based on the total weight of the cracking catalyst.

6. The process of claim 1, where the shape selective zeolite is ZSM-5 zeolite having a silica to alumina molar ratio of from 500 to 2000 where the silica to alumina molar ratio is defined as the moles of silica divided by the moles of alumina.

7. The process of claim 1, where the feed stream comprises 1-butene, 2-butene, isobutane, and n-butane, where the 2-butene comprises cis-2-butene and trans-2-butene.

8. The process of claim 1, where the feed stream comprises:
   from 12.5 weight percent to 50 weight percent 1-butene;
   from 12.5 weight percent to 25 weight percent 2-butenes; and
   from 15 weight percent to 25 weight percent isobutane.

9. The process of claim 1, where the zeolite particles comprise a phosphorous peptizer.

10. The process of claim 9, where the phosphorous peptizer comprises phosphoric acid.

11. The process of claim 1, comprising contacting the feed stream with the cracking catalyst at a temperature of from 300° C. to 650° C.

12. The process of claim 1, comprising contacting the feed stream with the cracking catalyst in a fixed bed reactor.

13. The process of claim 12, where the fixed bed reactor comprises a plurality of fixed bed reactors in parallel.

14. The process of claim 13, further comprising operating the plurality of fixed bed reactors in swing mode, where operating in swing mode comprises contacting the feed stream with the cracking catalyst in one of the plurality of fixed bed reactors and simultaneously regenerating, reconditioning, or replacing the cracking catalyst in another of the plurality of fixed bed reactors.

15. The process of claim 1, further comprising before contacting the feed stream with the cracking catalyst, contacting the feed stream with a metathesis catalyst in a metathesis reaction zone to produce a metathesis reaction product stream, and then contacting the metathesis reaction product stream with the cracking catalyst.

* * * * *